(12) United States Patent
Urbahns et al.

(10) Patent No.: US 6,339,083 B1
(45) Date of Patent: *Jan. 15, 2002

(54) MULTIHETEROCYCLIC PHARMACEUTICALS

(75) Inventors: Klaus Urbahns; Delf Schmidt, both of Wuppertal (DE); Ulf Brueggemeier, Madison, CT (US); Christoph Gerdes, Leverkusen (DE); Beatrix Stelte-Ludwig, Wülfrath (DE); Jörg Keldenich; Elke Stahl, both of Wuppertal (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 108 days.

(21) Appl. No.: 09/211,274

(22) Filed: Dec. 14, 1998

(51) Int. Cl.$^7$ .................. A61K 31/5513; C07D 243/14
(52) U.S. Cl. ................ 514/221; 540/504; 540/512; 540/513; 540/516
(58) Field of Search .............. 514/221; 540/504, 540/512, 513, 516

(56) References Cited

U.S. PATENT DOCUMENTS

| | | | |
|---|---|---|---|
| 5,403,836 A | 4/1995 | Blackburn et al. | 514/213 |
| 5,668,159 A | 9/1997 | Jin et al. | 514/363 |
| 5,977,101 A | * 11/1999 | Ali et al. | 514/221 |
| 6,008,214 A | 12/1999 | Kwon et al. | 514/211 |
| 6,069,158 A | 5/2000 | Miller et al. | 514/352 |

FOREIGN PATENT DOCUMENTS

| | | |
|---|---|---|
| WO | WO 94/14776 | 7/1994 |
| WO | WO 95/14683 | 6/1995 |
| WO | WO 96/00730 | 1/1996 |
| WO | WO 96/06087 | 2/1996 |
| WO | WO 96/14192 | 5/1996 |
| WO | WO 96/26190 | 8/1996 |
| WO | WO 97/01540 | 1/1997 |
| WO | WO 97/24119 | * 7/1997 |
| WO | WO 98/30542 | 7/1998 |

* cited by examiner

*Primary Examiner*—Bruck Kifle
(74) *Attorney, Agent, or Firm*—Norris McLaughlin & Marcus

(57) ABSTRACT

The present invention relates to compounds of the general formula (I):

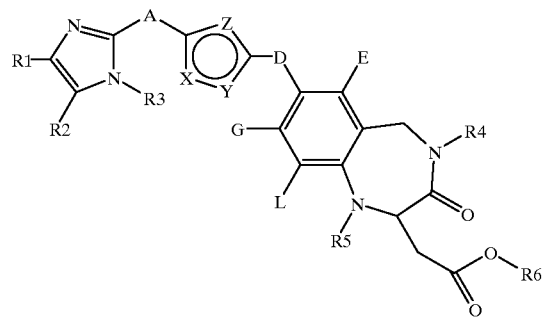

and their preparation and use for the production of pharmaceuticals, and pharmaceuticals comprising these compounds.

8 Claims, No Drawings

MULTIHETEROCYCLIC PHARMACEUTICALS

The present invention relates to new multiheterocyclic compounds with a broad spectrum of action having, inter alia, antiosteoporotic, antirestenotic, anticarcinogenic and antiatherosclerotic activity. The present invention moreover relates to the preparation of these compounds and their use for the production of medicaments, and also medicaments comprising them.

WO 97/24119 discloses antiosteoporosis agents which are structurally related to the compounds described here, but do not have a broad spectrum of action of this type.

The compounds on which the present invention is based can be described by the following general formula (I):

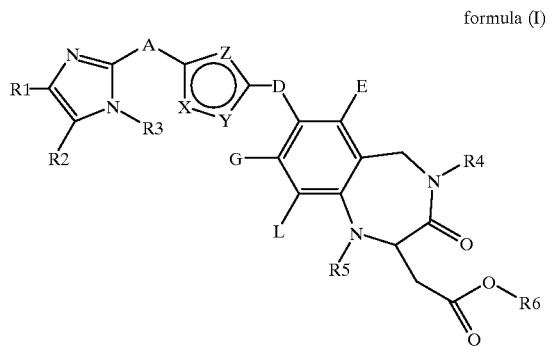

formula (I)

where
R1 and R2
  together with the formal double bond bridging them form a phenyl ring or a six-membered aromatic heterocycle having 1 or 2 nitrogen atoms, which is optionally substituted by halogen, nitro, cyano, trifluoromethyl, hydroxyl, $(C_1-C_6)$-alkyl, alkoxy, alkoxycarbonyl, amino, carboxyl, phenoxy, aryl, alkylamino, sulfone or sulfonamine, and
R3=
  H or $(C_1-C_4)$-alkyl, and
A=
  O, S, $(CH_2)_n$ where n=1,2,3 or 4 or N—R7 where R7=H or $(C_1-C_4)$-alkyl, or is absent and
X, Y, Z=
  O, S, N, N—R8 where R8=H, $(C_1-C_6)$-alkyl or aryl, or C—(R9)(R10) where R9, R10=H, $(C_1-C_6)$-alkyl or aryl, or C—(R11) if the X, Y or Z in question is participating in a formal double bond, where R11=H, $(C_1-C_6)$-alkyl or aryl, and
D=
  O, S, $(CH_2)_n$ where n=1,2,3 or 4, or N—R7 where R7=H or $(C_1-C_4)$-alkyl, or is absent and
E, G, L=
  H, halogen, nitro, cyano, trifluoromethyl, hydroxyl, carboxyl, $C_1-C_6$-alkyl, alkoxy or alkoxycarbonyl, where E, G and L can be identical or different and
R4=
  H, $(C_3-C_8)$-cycloalkyl, $(C_1-C_6)$-alkyl, which is optionally substituted by hydroxyl, $(C_1-C_6)$-alkoxy or phenyl, where the latter is optionally in turn substituted on the phenyl ring by halogen, $(C_1-C_4)$-alkyl, $(C_1-C_4)$-alkoxy, hydroxyl, trifluoromethoxy or trifluoromethyl, and
R5=
  H or $(C_1-C_4)$-alkyl and
R6=
  H, $(C_1-C_6)$-alkyl or benzyl.

Preferred compounds according to the general formula (I) are those where
R1 and R2
  together with the formal double bond bridging them form a phenyl ring or a six-membered aromatic heterocycle having 1 or 2 nitrogen atoms, which is optionally substituted by alkoxy or amino, and
R3=
  H, and
A=
  O, S, $(CH_2)_n$ where n=1,2,3 or 4 or N—H, or is absent and
X, Y, Z=
  O, S, N, N—R8 where R8=H, $(C_1-C_6)$-alkyl or aryl, or C—(R9)(R10) where R9, R10=H, $(C_1-C_6)$-alkyl or aryl, or C—(R11) if the X, Y or Z in question is participating in a formal double bond, where R11=H, $(C_1-C_6)$-alkyl or aryl, and
D=
  O, S, $(CH_2)_n$ where n=1,2, 3 or 4, or N—H, or is absent and
E, G, L=
  H, and
R4=
  H, benzyl, cyclopropyl, cyclopentyl, cyclohexyl, phenylethyl or $(C_1-C_4)$-alkyl, which is optionally substituted by hydroxyl or methoxy, and
R5=
  H, and
R6=
  H or methyl.

Particularly preferred compounds according to the general formula (I) are those where
R1 and R2
  together with the formal double bond bridging them form a phenyl ring, and
R3=
  H, and
A=
  is absent and
X=O, Y=N and Z=N or X=N, Y=N and Z=O, S and
D=
  is absent and
E, G, L=
  H, and
R4=
  methyl and
R5=
  H, and
R6=
  methyl.

The compounds of the general formula (I) according to the invention can be prepared in the following way using process variant (A) or (B):

(A) reaction of a component (a)

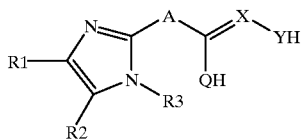

with a component (b)

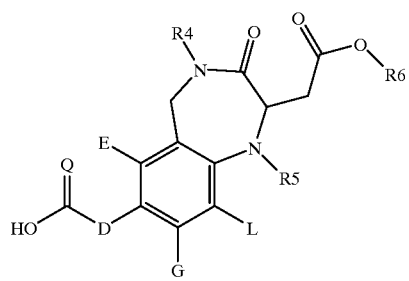

where b is first reacted in the presence of sulfonyl chloride, POCl$_3$ or PCl$_5$ to give the acid chloride and is then reacted with a in the presence of a base in an inert organic solvent, or a coupling of a with b is carried out by means of BOP or carbodiimide reagents, followed by a cyclization reaction which can be effected by means of heat, acids, bases, dehydrating substances and by addition of generally nucleophilic reagents, where, if appropriate, the COOR6 group is finally hydrolyzed and where Q in one of the two components (a) or (b) is oxygen and in the other components corresponds to Z, or (B) reaction of a component (a')

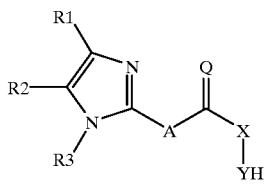

with a component (b)

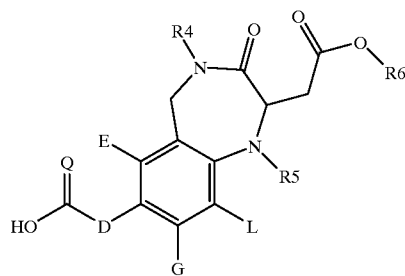

where b is first reacted in the presence of sulfonyl chloride, POCl$_3$ or PCl$_5$ to give the acid chloride and then reacted with a' in the presence of a base in an inert organic solvent, or a coupling of a' with b is carried out by means of BOP or carbodiimide reagents, followed by a cyclization reaction which can be effected by means of heat, acids, bases, dehydrating substances and by addition of generally nucleophilic reagents, where, if appropriate, the COOR6 group is finally hydrolyzed and where Q in one of the two components (a') or (b) is oxygen and in the other component corresponds to Z.

Preferably, in process variant (A), for component (a), X=N, Y=O and Q=NH is employed and for component (b), Q=O is employed and in process variant (B), for component (a'), X=NH, Y=NH and Q=O is employed and, for component (b'), Q=O is employed.

Particularly preferably, it applies to both process variants that R1 and R2 together with the formal double bond bridging them form a phenyl radical,

R3, R5, E, G, L=H,

R4, R6=methyl and

A, D=is absent.

The compounds of the formula (I) according to the invention have a surprisingly wide spectrum of pharmacological action.

They can be used as active compounds in medicaments for the reduction of changes to vascular walls and are employed for the treatment of arterial hypertension and atherosclerosis. Moreover, they can be employed for the treatment of coronary heart disorders, cardiac insufficiency, disorders of brain function, ischemic brain disorders, (peripheral) circulation disorders, micro-circulation disorders and thromboses, functional disorders of the kidney and adrenal gland, bronchospastic and vascular system-related disorders of the airways, sodium retention and edemas as well as osteoporosis and carcinoses.

Furthermore, the proliferation and migration of smooth muscle cells plays a decisive part in the occlusion of vessels. The compounds according to the invention are suitable for inhibiting this proliferation and can therefore also be employed for the treatment of restenosis.

The novel active compounds are distinguished pharmacologically by good kinetic parameters. In particular, they have favorable properties with respect to clearance.

The novel active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this case the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if water is used as a diluent organic solvents can optionally be used as auxiliary solvents.

Administration is carried out in a customary manner, preferably orally or parenterally, in particular perlingually or intravenously.

In the case of parenteral administration, solutions of the active compound using suitable liquid carrier materials can be employed.

In general, it has proven advantageous in the case of intravenous administration to administer amounts from approximately 0.001 to 1 mg/kg, preferably approximately 0.01 to 0.5 mg/kg, of body weight to achieve effective results, and in the case of oral administration the dose is approximately 0.01 to 100 mg/kg, preferably 0.1 to 50 mg/kg, of body weight.

In spite of this, if appropriate, it may be necessary to depart from the amounts mentioned, namely depending on the body weight or the type of application route, on individual behavior toward the medicament, the manner of its formulation and the time or interval at which administration takes place. Thus in some cases it may be adequate to manage with less than the abovementioned minimum amount, while in other cases the upper limits mentioned must be exceeded. In the case of the administration of relatively large amounts, it may be advisable to divide these into several individual doses over the course of the day.

The present invention is illustrated in greater detail below by working examples.

Starting Compound I

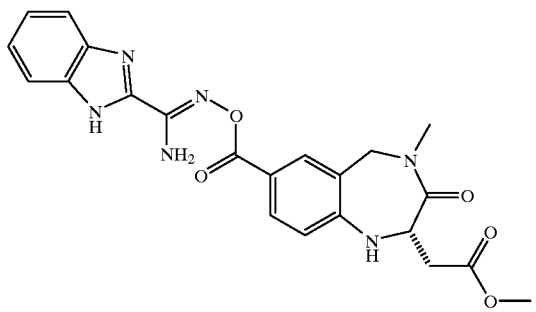

S—O-{(4-Methyl-3-oxo-2,3,4,5-tetrahydro-1H-benzol[e][1,4]diazepine-2-methoxycarbonylmethyl)-7-oyl}benzimidazole-2-carboxamidoxime 0.877 g of methyl S-7-carboxy-2,3,4,5-tetrahydro-4-methyl-3-oxo-1H-1,4-benzodiazepine-2-acetate (Tetrahedron Letters 38, 3131–34, 1997) is stirred under reflux for 1 h with thionyl chloride (40 ml), concentrated and the residue is dissolved in 20 ml of chloroform. The solution obtained is added dropwise to a mixture of 0.53 g of benzimidazole-2-carboxamidoxime (J. Chem. Soc. C, 1967, 28) and chloroform (50 ml), pyridine (0.48 g) and triethylamine (0.30 g). It is stirred at room temperature for 2 h, then concentrated and the residue is taken up in ethyl acetate. After this, washing with water, saturated sodium hydrogencarbonate solution and saturated sodium chloride solution and drying over magnesium sulfate takes place, after concentration an amorphous residue being obtained which is stirred with dichloromethane and filtered off with suction. Recrystallization is carried out from ethanol (0.41 g). The mother liquor is concentrated and chromatographically purified ($CH_2Cl_2$; $CH_2Cl_2/CH_3OH$=30/1). 0.6 g of the title compound is obtained from the mother liquor.

PREPARATION EXAMPLE 1

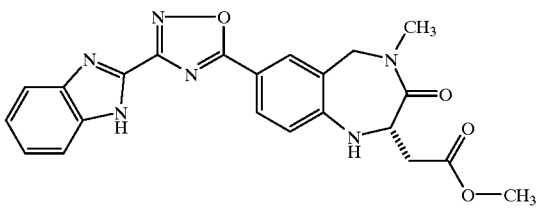

S-Methyl 7-[3-(1H-benzimidazol-2-yl)-[1,2,4]oxadiazol-5-yl]-4-methyl-3-oxo-2,3,4,5-tetrahydro-1H-benzo[e][1,4]diazepine-2-acetate Starting Compound I (900 mg) is dissolved in 20 ml of dimethylformamide and treated with 3 ml of pyridine. The mixture is refluxed for 20 h. It is then treated with water and extracted 3 times with ethyl acetate. Washing with saturated sodium chloride solution and drying over magnesium sulfate yield, after concentration, a residue which is purified by means of flash chromatography (flash chrom. $CH_2Cl_2$; $CH_2Cl_2$/ethyl acetate=1/1; $CH_2/Cl_2$/ethyl acetate/methanol= 20/20/1). The fractions are concentrated after TLC and the residue is recrystallized from ethyl acetate/diethyl ether. 256 mg of the title compound are obtained.

PREPARATION EXAMPLE 2

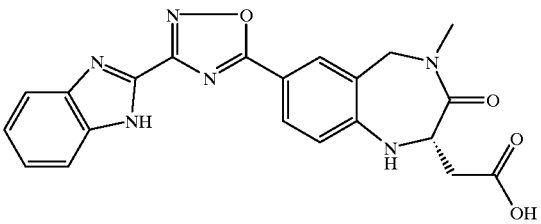

S-{7-[3-(1H-Benzimidazol-2-yl)-[1,2,4]oxadiazol-5-yl]-4-methyl-3-oxo-2,3,4,5-tetrahydro-1H-benzo[e][1,4]diazepin-2-yl}-acetic acid 238 mg of the compound from Preparation Example 1 are dissolved in 10 ml of dimethoxyethane and 8 ml of water. The mixture is then treated with 10 mg of LiOH×$H_2O$ and stirred at room temperature for 2 h. It is extracted twice with ether, the aqueous phase is acidified with acetic acid and the precipitating product is filtered off with suction. The solid is washed with water, dissolved in 150 ml of dichloromethane/methanol/ethanol (1/1/1) and concentrated to 5 ml. The solid obtained is washed with ether (yield: 183 mg). $^1$H NMR (200 MHz, DMSO): 2.59 (1 H, dd J=8 Hz), 2.80 (1H, dd, 10 Hz, 17.5 Hz), 2.94 (s, 3H), 4.03 (d, 1H, 17.5 Hz), 5.21 (m, 1H), 5.52 (d, 1H, 17.5 Hz), 6.73 (d, 1H, 7.5 Hz), 6.93 (s, 1H), 7.15–7.90 (m, 7H), 13.5 (broad s, 1H).

Starting Compound II

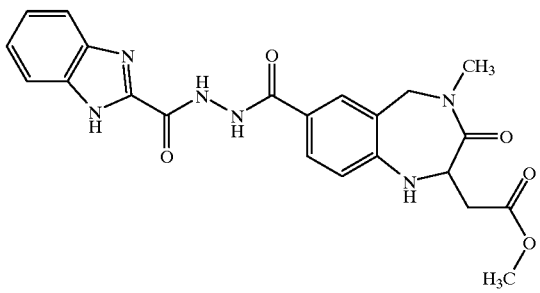

Methyl 7-[N'-(1H-benzimidazole-2-carbonyl)-hydrazinocarbonyl]-4-methyl-3-oxo-2,3,4,5-tetrahydro-1H-benzo[e][1,4]diazepine-2-acetate Methyl 7-carboxy-2,3,4,5-tetrahydro-4-methyl-3-oxo-1H-1,4-benzodiazepine-2-acetate (292 mg) is heated under reflux in 10 ml of thionyl chloride. After this, the mixture is concentrated and the residue is taken up in 10 ml of chloroform. This solution is added dropwise at 0° C. to a mixture of benzimidazole-2-carboxyhydrazide (176 mg), chloroform (30 ml) and pyridine (1 ml). The mixture is stirred for 1 h at 0° C. and for 2 h at room temperature. It is then concentrated again, and the residue is purified by chromatography ($CH_2Cl_2$/methanol=20+1). Recrystallization from ethanol yields 194 mg of yellow crystals.

PREPARATION EXAMPLE 3

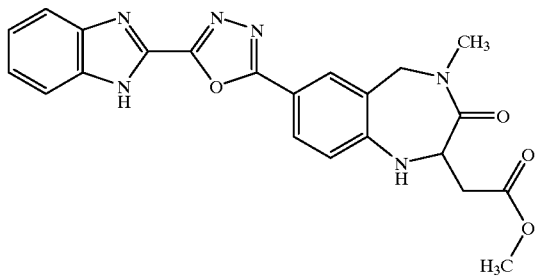

Methyl 7-[5-(1H-benzimidazol-2-yl)-[1,3,4]oxadiazol-2-yl]-4-methyl-3-oxo-2,3,4,5-tetrahydro-1H benzo[e][1,4]diazepine-2-acetate 90 mg of the Starting Compound II are introduced into 15 ml of tetrahydrofuran and treated with 0.2 ml of thionyl chloride. After reflux for 2 h, the mixture is concentrated and the residue is recrystallized from ethanol. The mother liquor is concentrated and purified by chromatography ($CH_2Cl_2$/ethyl acetate gradient). The product crystallizes from dichloromethane (yield: 10 mg).

PREPARATION EXAMPLE 4

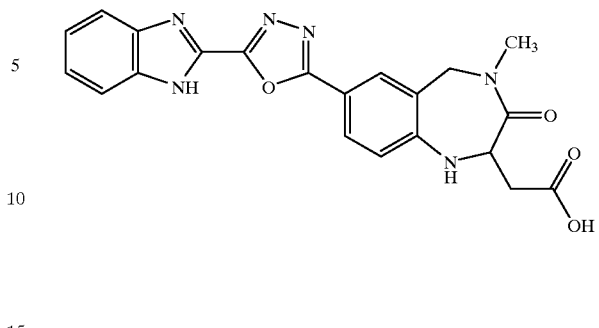

{7-[5-(1H-benzimidazol-2-yl)-[1,3,4]oxadiazol-2-yl]-4-methyl-3-oxo-2,3,4,5-tetrahydro-1H-benzo[e][1,4]diazepin-2-yl}-acetic acid 200 mg of the compound from Preparation Example 3 are treated analogously to Preparation Example 2. 141 mg of the title compound are obtained. $^1$H NMR (200 MHz, DMSO): 2.49 (1 H, dd J=5.5 Hz, J=17.5), 2.62 (1H, dd, 8.5 Hz, 17.5 Hz), 2.96 (s, 3H), 3.5 (broad s, 1H), 4.05 (d, 1H, 16.0 Hz), 5.17 (m, 1H), 5.52 (d, 1H, 16.0 Hz), 6.73 (d, 1H, 16.0 Hz), 6.85 (s, 1H), 7.30 (m, 2 H), 7.15–7.70 (m, 5H).

PREPARATION EXAMPLE 5

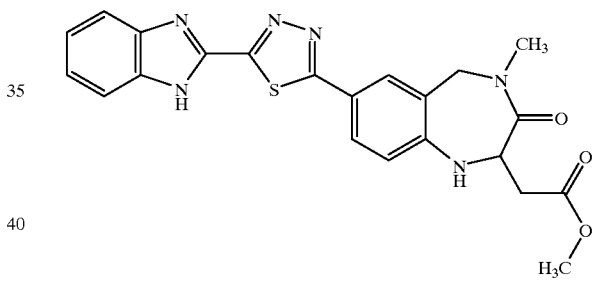

Methyl 7-[5-(1H-benzimidazol-2-yl)-[1,3,4]thiadiazol-2-yl]-4-methyl-3-oxo-2,3,4,5-tetrahydro-1H-benzo[e][1,4]diazepine-2-acetate 900 mg of the compound from Starting Compound II are dissolved in 60 ml of THF and treated with 1.2 g of Lawesson's reagent. The mixture is stirred under reflux for 3 h. The crystalline product is filtered off with suction and washed with methylene chloride/diethyl ether (yield: 1.65 g).

An analytical sample is obtained by preparative HPLC. Yellow crystals.

$^1$H NMR (200 MHz, DMSO): 2.67 (1 H, dd J=6 Hz, 17.5 Hz), 2.88 (1H, dd, 10 Hz, 17.5 Hz), 2.96 (s, 3H), 3.62 (s, 3H), 4.07 (d, 1H, 17.5 Hz), 5.22 (m, 1H), 5.51 (d, 1H, 17.5 Hz), 6.65–6.72 (m, 2H), 7.20–7.38 (m, 2H), 7.57 (d, 1H, 7.5 Hz), 7.60–7.80 (m, 3H).

PREPARATION EXAMPLE 6

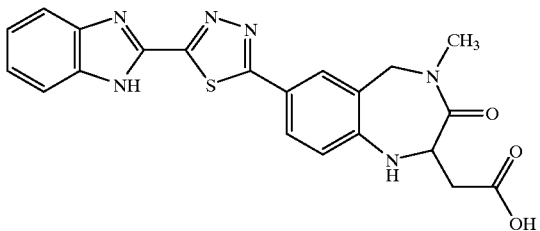

{7-[5-(1H-Benzimidazol-2-yl)-[1,3,4]thiadiazol-2-yl]-4-methyl-3-oxo-2,3,4,5-tetrahydro-1H-benzo[e][1,4]diazepin-2-yl}-acetic acid 50 mg of the compound from Preparation Example 5 are treated analogously to Preparation Example 2. 33 mg are obtained as a yellow solid. $^1$H NMR (200 MHz, DMSO): 2.72 (1 H, dd J=7.5 Hz, J=17.5), 2.62 (1H, concealed by water signal), 2.95 (s, 3H), 4.06 (d, 1H, 16.2 Hz), 5.13 (m, 1H), 5.51 (d, 1H, 16.2 Hz), 6.70 (d, 1H, 9 Hz) under: 6.80 (s, broad, 1H), 7.31 (m, 2H), 7.60–7.80 (m, 4H), 13.8 (s, broad, 1H).

Starting Compound III

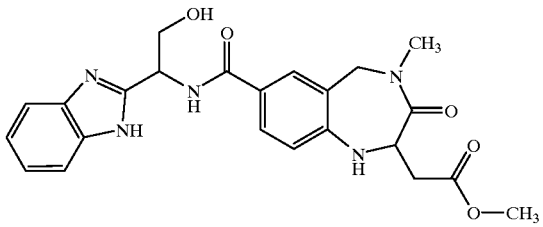

Methyl {7-[1-(1H-benzimidazol-2-yl)-2-hydroxy-ethylcarbamoyl]-4-methyl-3-oxo-2,3,4,5-tetrahydro-1H-benzo[e][1,4]diazepin-2-yl}-acetate 0.75 g of 2-amino-2-(1H-benzimidazol-2-yl)-ethanol.HCl (Maekawa; Ohtani, Agric. Biol. Chem., 40, 1976, 791) and 0.88 g of methyl 7-carboxy-2,3,4,5-tetrahydro-4-methyl-3-oxo-1H-1,4-benzodiazepine-2-acetate are dissolved in 30 ml of DMF and treated with 0.49 g of 1-hydroxybenzotriazole and 0.58 g of N'-(3-dimethylaminopropyl)-N-ethylcarbodiimide.hydrochloride and 1.55 g of diisopropylethylamine.

The mixture is stirred for 20 h and partitioned between ethyl acetate and water. Extraction 3 times with ethyl acetate and washing of the organic phase with water and saturated sodium chloride solution and subsequent drying over magnesium sulfate and concentration yields a residue which crystallizes using ethyl acetate. 521 mg are obtained from the first crystallizate and 158 mg from the mother liquor.

PREPARATION EXAMPLE 7

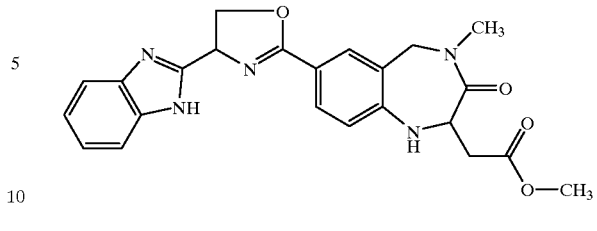

Methyl 7-[4-(1H-benzimidazol-2-yl)-4,5-dihydro-oxazol-2-yl]-4-methyl-3-oxo-2,3,4,5-tetrahydro-1H-benzo[e][1,4]diazepine-2-acetate 410 mg of the Starting Compound III are dissolved in 60 ml of tetrahydrofuran and reated with 320 mg of (methoxycarbonylsulfamoyl)-triethylammonium-N-betaine (Burgess reagent). The mixture is heated under reflux for 2 h, concentrated, and partitioned between ethyl acetate and water. Purification on 20 g of silica gel (CH$_2$Cl$_2$/AcOEt/MeOH=40+40+1) leads to 163 mg of gray solid.

$^1$H NMR (200 MHz, CDCl$_3$): 2.68 (dd, 1 H, J=16.0, 6.5) 2.99, 3.10 (each 1 s, 3H) under: 3.0 dd 1H J=16.0, 5.5), 3.66 (1H, dd, 17.5 Hz, 9.0 Hz), 3.76 (s, 3H), 4.59 (m, 1H), 4.78–4.99 (m, 2H), 5.11 (m, 1H), 5.29–5.49 (m, 1H), 5.70 (m, 1H), 6.52 (m, 1H), 7.2–7.8 (m, 7H).

PREPARATION EXAMPLE 8

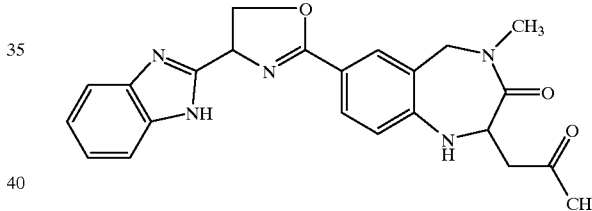

{7-[4-(1H-Benzimidazol-2-yl)-4,5-dihydro-oxazol-2-yl]-4-methyl-3-oxo-2,3,4,5-tetrahydro-1H-benzo[e][1,4]diazepin-2-yl}-acetic acid Analogously to Preparation Example 2, 30 mg of the compound from Preparation Example 7 are dissolved in 5 ml of 1,2-dimethoxyethane and treated with 3 ml of water. 17 mg of slightly reddish crystals are obtained. $^1$H NMR (200 MHz), DMSO): 2.55 (dd, 1H, 5 Hz, 17.5 Hz); 2.79 (dd, 1H, 8.5 Hz, 17.5 Hz); 3.35 (s, 3H), 3.90 (d, 1H, 17.7 Hz), 4.62–4.82 (m, 2H), 5.11 (m, 1H), 5.92–5.61 (m, 2H), 6.47 (d, 1H, 3.75 Hz), 6.61 (d, 1H, 9.5 Hz), 7.15 (m, 2H), 7.42–7.62 (m, 4H), 12.30 (m, 1H), 12.48 (m, 1H).

Starting Compound IV

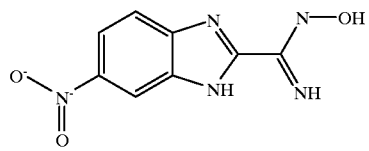

5-Nitro-benzimidazole-2-carboxamide oxime: (Starting compound IV)

2 g of 5-nitrobenzimidazole-2-carbonitrile (Lopyrev, V. A.; Larina, L. I.; Baumane, L. Kh.; Shibanova, E. F.; Gavar, R. A.; et al., Chem. Heterocycl. Compd. (Engl. Transl.), EN, 20, 9, 1984, 1021–1026, KGSSAQ, RU, 20, 9, 1984, 1246–1251) are dissolved in 60 ml of ethanol/water (5/1) and treated with 0.74 g of hydroxylammonium chloride and also 1.05 g of sodium acetate and refluxed for 2 h. The mixture is poured into ice water, and the brown precipitate is filtered off with suction and washed with water. 1.6 g of the title compound are obtained.

Starting Compound V

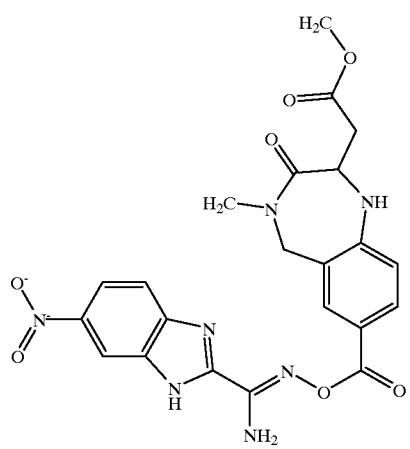

S-O-{(4-Methyl-3-oxo-2,3,4,5-tetrahydro-1H-benzo[e][1,4]diazepine-2-methoxycarbonylmethyl)-7-oyl}-5-nitro-benzimidazole-2-carboxamidoxime 670 mg of 5-nitro-benzimidazol-2-carboxamidoxime are reacted with 880 mg of methyl S-7-carboxy-2,3,4,5-tetrahydro-4-methyl-3-oxo-1H-1,4-benzodiazepine-2-acetate analogously to Starting Compound I. 800 mg of solid are obtained. MS (ESI) 496 (M+H)

PREPARATION EXAMPLE 9

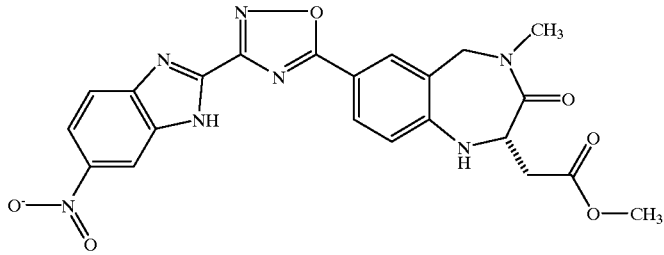

S-Methyl 7-[3-(5-nitro-1H-benzimidazol-2-yl)-[1,2,4]oxadiazol-5-yl]-4-methyl-3-oxo-2,3,4,5-tetrahydro-1H-benzo[e][1,4]diazepine-2-acetate 800 mg of S-O-{(4-methyl-3-oxo-2,3,4,5-tetrahydro-1H-benzo[e][1,4]diazepine-2-methoxycarbonylmethyl)-7-oyl}benzimidazole-2-carboxamidoxime are reacted analogously to Starting Compound II. Colorless solid. MS (ESI): 478 (M+H).

PREPARATION EXAMPLE 10

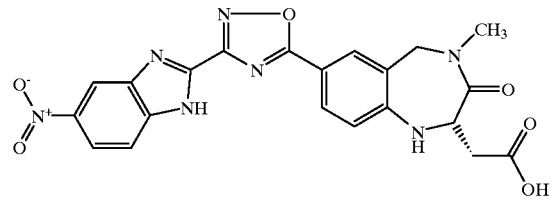

S-7-[3-(5-Nitro-1H-benzimidazol-2-yl)-[1,2,4]oxadiazol-5-yl]-4-methyl-3-oxo-2,3,4,5-tetrahydro-1H-benzo[e][1,4]diazepine-2-acetic acid 40 mg of S-methyl 7-[3-(5-nitro-1H-benzimidazol-2-yl)-[1,2,4]oxadiazol-5-yl]-4-methyl-3-oxo-2,3,4,5-tetrahydro-1H-benzo[e][1,4]diazepine-2-acetate are reacted analogously to Preparation Example 2. 11 mg of yellow solid. $^1$H NMR (400 MHz, DMSO): 2.61 (1 H, dd, J=8 Hz, 18.0 Hz), 2.79 (1H, dd, 10 Hz, 18.0 Hz), 2.96 (s, 3H), 4.03 (d, 1H, 18.0 Hz), 5.22 (m, 1H), 5.53 (d, 1H, 18.0 Hz), 6.75 (d, 1H, 10 Hz), 6.88 (m, 1H), 7.15–8.53 (m, 5H).

Starting Compound VI

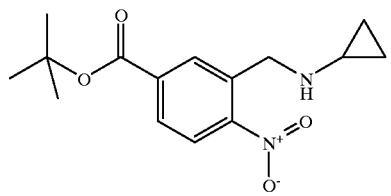

tert-Butyl 3-(cyclopropylamino)methyl-4-nitrobenzoate 23.7 g of tert-butyl 3-(bromomethyl)-4-nitrobenzoate are suspended in 400 ml of EtOH and treated at 0° C. with 9.0 g of cyclopropylamine. The mixture is stirred for 24 h, concentrated, and the residue is crystallized from petroleum ether. The mother liquor is chromatographed and crystallized. 19 g of the title compound are obtained. MS (DCI) 293 (M+H).

Starting Compound VII

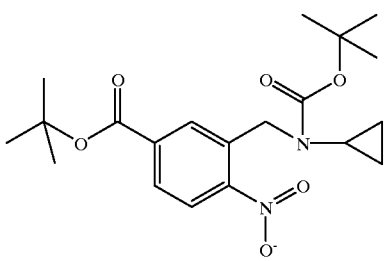

tert-Butyl 3-(N-cyclopropyl-N-tert-butoxycarbonyl)aminomethyl-4-nitrobenzoate

14.8 g of tert-butyl 3-(cyclopropylamino)methyl-4-nitrobenzoate are dissolved in 150 ml of ethyl acetate and treated with 12.1 g of di-tert-butyl dicarbonate. After aqueous working-up and chromatography (petroleum ether/ethyl acetate gradient), 20 g of product are obtained. MS (ESI) 393 (M+H)
Starting Compound VIII

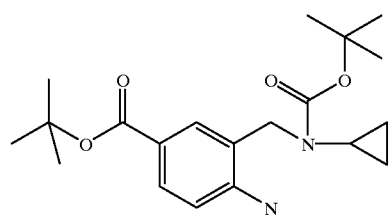

tert-Butyl 3-(N-cyclopropyl-N-tert-butoxycarbonyl)aminomethyl-4-aminobenzoate

4.9 g of tert-butyl 3-(N-cyclopropyl-N-tert-butoxycarbonyl)aminomethyl-4-nitrobenzoate in 100 ml of ethyl acetate are reduced using 1 g of Pd/C at normal pressure. 4.5 g are obtained as a colorless solid. MS (DCI) 363 (M+H)
Starting Compound IX

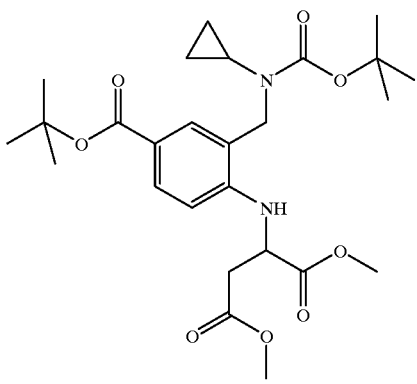

tert-Butyl 4-[2-(1,4-dimethoxy-dioxobutyl)amino]-3-[[N-3-cyclopropyl-N-tert-butoxycarbonyl)]amino]methylbenzoate

17.7 g of tert-butyl 3-(N-cyclopropyl-N-tert-butoxycarbonyl)aminomethyl-4-aminobenzoate are heated under reflux with 7.6 g of dimethyl acetylenedicarboxylate in 180 ml of MeOH. After 12 h, the mixture is concentrated, and the material obtained (26 g) is dissolved in methanol/ethyl acetate (1/1) and reduced using 1 g of Pd/C at room temperature at a pressure of 1 bar of hydrogen. Filtering off the catalyst with suction, concentration and chromatography (methylene chloride/ethyl acetate gradient) yield 19 g of the title compound as a colorless oil. MS (ESI) 507 (M+H)
Starting Compound X

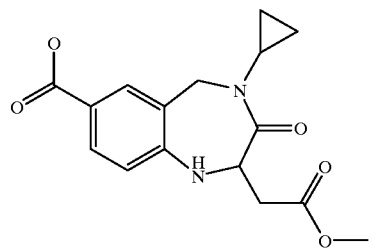

O-{(4-Cyclopropyl-3-oxo-2,3,4,5-tetrahydro-1H-benzo[e][1,4]diazepine-2-methoxycarbonylmethyl)-7-oyl}benzimidazole-2-carboxyamidoxime

19.1 g of tert-butyl 4-[2-(1,4-dimethoxy-dioxobutyl)amino]-3-[[N-3-cyclopropyl-N-tert-butoxycarbonyl)]amino]methylbenzoate are dissolved in 200 ml of methylene chloride and treated at 0° C. with 80 ml of trifluoroacetic acid. After stirring at room temperature for 12 h, the mixture is concentrated, taken up in 200 ml of MeOH, and treated at −5° with 10.3 ml of trifluoroacetic acid and 65 ml of 30% methanolic sodium methoxide solution. After standing at room temperature for 2 d, the mixture is treated with 6 ml of acetic acid and 80 ml of water with ice-cooling. The precipitation of pale yellow solid is completed by means of half-concentrated hydrochloric acid (to pH 4.5) and it is filtered off with suction. 5.8 g of the title compound are obtained. MS (DCI): 319 (M+H).
Starting Compound XI

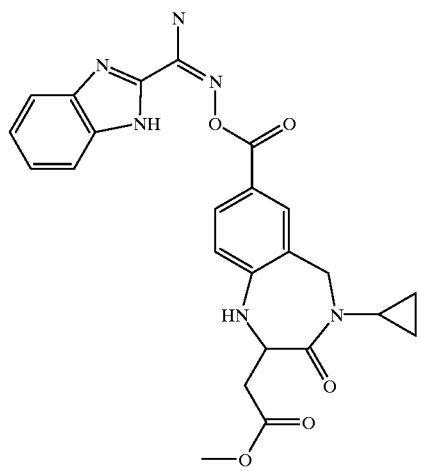

O-{(4-Cyclopropyl-3-oxo-2,3,4,5-tetrahydro-1H-benzo[e][1,4]diazepine-2-methoxycarbonylmethyl)-7-oyl}benzimidazole-2-carboxamidoxime

Analogously to Starting Compound I, 0.95 g of methyl 7-carboxy-4-cyclopropyl-2,3,4,5-tetrahydro-3-oxo-1H-1,4- benzodiazepine-2-acetate is reacted with 0.53 g of benzimidazole-2-carboxamide oxime. 0.9 g of the title compound is obtained. MS (ESI): 477 (M+H).

PREPARATION EXAMPLE 11

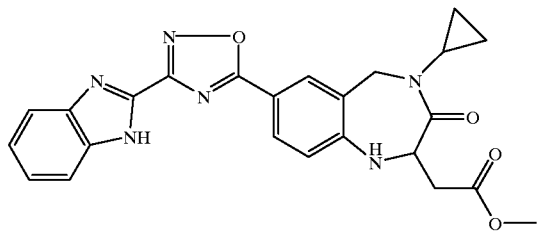

Methyl 7-[3-(1H-benzimidazol-2-yl)-[1,2,4] oxadiazol-5-yl]-4-cyclopropyl-3-oxo-2,3,4,5-tetrahydro-1H-benzo[e][1,4]diazepine-2-acetate 900 mg of O-{(4-cyclopropyl-3-oxo-2,3,4,5-tetrahydro-1H-benzo[e][1,4]diazepine-2-methoxycarbonylmethyl)-7-oyl}benzimidazole-2-carboxamidoxime in 20 ml of DMF and 3 ml of pyridine are heated under reflux (analogously to Example 2). Chromatography (methylene chloride/ethyl acetate/methanol, 40/40/1) and crystallization from methylene chloride/diethyl ether yield 135 mg of yellow crystals. MS (ESI): 459 (M+H).

PREPARATION EXAMPLE 12

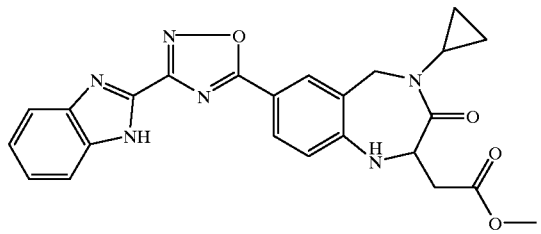

7-[3-(1H-Benzimidazol-2-yl)-[1,2,4]oxadiazol-5-yl]-4-cyclopropyl-3-oxo-2,3,4,5-tetrahydro-1H-benzo[e][1,4]diazepine-2-acetic acid 130 mg of methyl 7-[3-(1H-benzimidazol-2-yl)-[1,2,4]oxadiazol-5-yl]-4-cyclopropyl-3-oxo-2,3,4,5-tetrahydro-1H-benzo[e][1,4]diazepine-2-acetate are hydrolyzed in 4 ml of ethylene glycol dimethyl ether and 3 ml of water and also 90 mg of LiOH analogously to Preparation Example 2. 80 mg are obtained as a colorless solid. $^1$H NMR (400 MHz, DMSO): 0.59 (m, 1H), 0.77 (m, 1H), 2.58 (1 H, dd, J=5.2 Hz, 16.7 Hz) 2.75–2.85 (m, 2H), 2.96 (s, 3H), 4.09 (d, 1H, 16.9 Hz), 5.13 (m, 1H), 5.47 (d, 1H, 16.9 Hz), 6.76 (d, 1H, 8.6 Hz), 6.92 (m, 1H), 7.25–7.90 (m, 6H), 12.5 (broad s, 1H), 13.52 (m, 1H).

PREPARATION EXAMPLE XIII

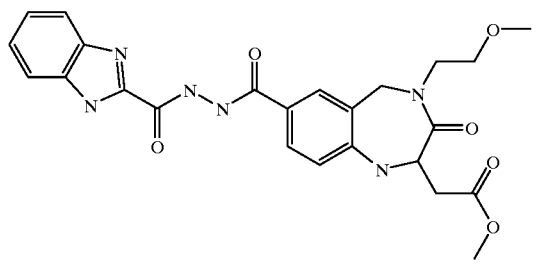

Methyl 7-[N'-(1H-benzimidazole-2-carbonyl)-hydrazinocarbonyl]-4-(2-ethoxy-ethyl)-3-oxo-2,3,4,5-tetrahydro-1H-benzo[e][1,4]diazepine-2-acetate 1130 mg of methyl 7-carboxy-2,3,4,5-tetrahydro-4-(2-methoxyethyl)-3-oxo-1H-1,4-benzodiazepine-2-acetate (1130 mg, preparation analogously to Example 12 using methoxyethylamine) are heated under reflux in 10 ml of thionyl chloride. The mixture is concentrated and the residue is taken up in 50 ml of CHCl$_3$. This solution is added dropwise at 0° C. to a mixture of benzimidazole-2-carboxyhydrazide (510 mg) in CHCl$_3$ (100 ml) and pyridine (2 ml). The mixture is then stirred for 1 h at 0° C. and for 2 h at room temperature. It is then concentrated, and the residue is purified by chromatography (CH$_2$Cl$_2$/MeOH=20+1). Recrystallization from EtOH/AcOEt/Et$_2$O yields 488 mg of yellow crystals. R$_f$=0.25 (CH$_2$Cl$_2$/CH$_3$OH=10:1)

PREPARATION EXAMPLE 13

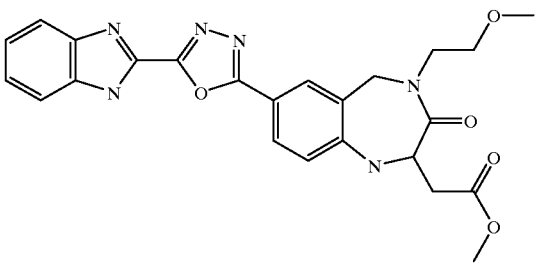

Methyl 7-[5-(1H-benzimidazol-2-yl)-[1,3,4] oxadiazol-5-yl]-4-(2-methoxyethyl)-3-oxo-2,3,4,5-tetrahydro-1H-benzo[e][1,4]diazepine-2-acetate 450 mg of the substance from Example 10 are introduced into 200 ml of THF and treated with 0.8 ml of thionyl chloride. After heating under reflux for 2 h, the mixture is concentrated and the residue is partitioned between AcOEt/NaHCO$_3$ solution. The organic phase is separated off, and washed successively with water and saturated sodium chloride solution. It is dried over MgSO$_4$ and purified by chromatography (CH$_2$Cl$_2$, AcOEt gradient). The product crystallizes from dichloromethane/EtOH (350 mg). R$_f$=0.40 (CH$_2$Cl$_2$/CH$_3$OH=10:1).

PREPARATION EXAMPLE 14

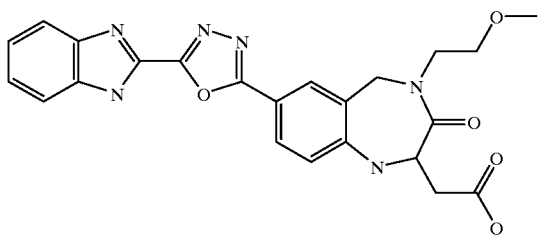

{7-[5-(1H-benzimidazol-2-yl)-[1,3,4]oxadiazol-2-yl]-4-(2-methoxyethyl-3-oxo-2,3,4,5-tetrahydro-1H-benzo[e][1,4]diazepin-2-yl}-acetate 80 mg of the compound from Example 14 are treated analogously to Preparation Example 3. 63 mg of the title compound are obtained ($R_f$=0.42 $CH_2Cl_2/CH_2OH$=3+1: Example 14: Rf=0.90). $^1$H NMR (200 MHz, DMSO): 2.58 (1H, dd J=5.0 Hz, J=17.0), 2.82 (1H, dd, 9.0 Hz, 17.0 Hz), 3.12 (s, 3H), 3.20–3.70 (m, 5H), 4.18 (d, 1H, 16.0 Hz), 5.20 (m, 1H), 5.51 (d, 1H, 16.0 Hz), 6.69 (s, 1H,) 6.79 (s, 1H), 7.25–7.40 (m, 2H), 7.60–7.84 (m, 4H), 12.4 (br., 1H), 13.8 (br., 1H).

The substances were tested for their ability to inhibit $\alpha_v\beta_3$/echistatin binding analogously to Kumar C. C., Nie H. M., Rogers G. P., Malkowski M., Maxwell E., Catino J. J. and Armstrong L. (Journal of Pharmacology and Experimental Therapeutics 283 (2) (1997) 843–853).

$\alpha_v\beta_3$ Test $\alpha_v\beta_3$ from human placenta (Smith J. W. and Cheresh, D. A. (1988), J. Biol. Chem. 263, 18726–18732) (1 mg/ml 50 mM tris HCl pH 7.4, 100 mM NaCl, 2 mM $CaCl_2$, 1% and octylglucoside) was diluted with test buffer (50 mM tris-HCl pH 7.4, 100 mM NaCl, 1 mM $CaCl_2$, 1 mM $MgCl_2$, 1 mM $MnCl_2$, 0.1% bovine serum albumin) and 55 µl each of this $\alpha_v\beta_3$ solution were added to the wells of a 96-well microtiter plate (about 0.1–0.3 µg of $\alpha_v\beta_3$ per well). 2 µl of the substances to be tested dissolved in DMSO were then added. 10 µl (40,000 cpm) of $I^{125}$-echistatin per well were then added and the mixture was incubated for 1 hour at room temperature with careful shaking. It was then treated with 100 µg of wheatgerm-coated yttrium silicate beads (Amersham, type RPNQ0011) in 25 µl of distilled water. After 1 hour at room temperature, the cpm values were measured in a scintillation counter. The $IC_{50}$ values were determined in duplicate from concentration series. The non-specific binding was determined in the presence of 0.1 µM unlabeled echistatin or by addition of 5 mM EDTA to the binding mixture.

What is claimed is:

1. A compound of the formula (I):

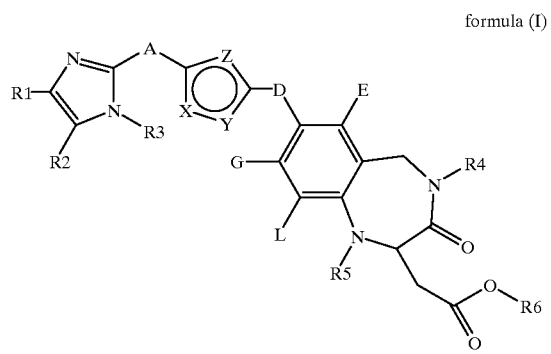

formula (I)

where

R1 and R2
together with the formal double bond bridging them form a phenyl ring or a six-membered aromatic heterocycle having 1 or 2 nitrogen atoms, which is optionally substituted by halogen, nitro, cyano, trifluoromethyl, hydroxyl, ($C_1$–$C_6$)-alkyl, alkoxy, alkoxycarbonyl, amino, carboxyl, phenoxy, aryl, alkylamino, sulfone and sulfonamine, and R3=
H or ($C_1$–$C_4$)-alkyl, and A=
O, S, $(CH_2)_n$ where n=1,2,3 or 4 or N—R7 where R7=H or ($C_1$–$C_4$)-alkyl, or is absent and X, Y, Z=
O, S, N, N—R8 where R8=H, ($C_1$–$C_6$)-alkyl or aryl, or C—(R9)(R10) where R9, R10=H, ($C_1$–$C_6$)-alkyl or aryl, or C—(R11) if the X, Y or Z in question is participating in a formal double bond, where R11=H, ($C_1$–$C_6$)-alkyl or aryl, and D=
O, S, $(CH_2)_n$ where n=1,2,3 or 4, or N—R7 where R7=H or ($C_1$–$C_4$)-alkyl, or is absent and E, G, L=
H, halogen, nitro, cyano, trifluoromethyl, hydroxyl, carboxyl, ($C_1$–$C_6$)-alkyl, alkoxy or alkoxycarbonyl, where E, G and L can be identical or different and R4=
H, ($C_3$–$C_8$)-cycloalkyl, ($C_1$–$C_6$)-alkyl, which is optionally substituted by hydroxyl, ($C_1$–$C_6$)-alkoxy or phenyl, where the latter is optionally in turn substituted on the phenyl ring by halogen, ($C_1$–$C_4$)-alkyl, ($C_1$–$C_4$)-alkoxy, hydroxyl, trifluoromethoxy or trifluoromethyl, and R5=
H or ($C_1$–$C_4$)-alkyl and R6=
H, ($C_1$–$C_6$)-alkyl or benzyl.

2. A compound of the formula (I) as claimed in claim 1, wherein

R1 and R2
together with the formal double bond bridging them form a phenyl ring or a six-membered aromatic heterocycle having 1 or 2 nitrogen atoms, which is optionally substituted by alkoxy or amino, and

R3=

H, and

A=

O, S, (CH$_2$)$_n$ where n=1,2,3 or 4 or N—H, or is absent and

X, Y, Z=

O, S, N, N—R8 where R8=H, (C$_1$–C$_6$)-alkyl or aryl, or C—(R9)(R10) where R9, R10=H, (C$_1$–C$_6$)-alkyl or aryl, or C—(R11) if the X, Y or Z in question is participating in a formal double bond, where R11=H, (C$_1$–C$_6$)-alkyl or aryl, and

D=

O, S, (CH$_2$)$_n$ where n=1, 2, 3 or 4, or N—H, or is absent and

E, G, L=

H, and

R4=

H, benzyl, cyclopropyl, cyclopentyl, cyclohexyl, phenylethyl or (C$_1$–C$_4$)-alkyl, which is optionally substituted by hydroxyl or methoxy, and

R5=

H, and

R6=

H or methyl.

3. A compound of the formula (I) as claimed in claim 1, wherein

R1 and R2 together with the formal double bond bridging them form a phenyl ring, and

R3=

H, and

A= is absent and

X=O, Y=N and Z=N or X=N, Y=N and Z=O, S and

D= is absent and

E, G, L=

H, and

R4= methyl and

R5=

H, and

R6= methyl.

4. A process for the preparation of the compounds of the formula (I) as claimed in claim 1, which comprises obtaining these by (A) reaction of a component (a)

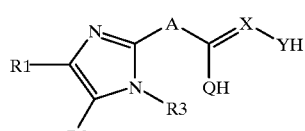

with a component (b)

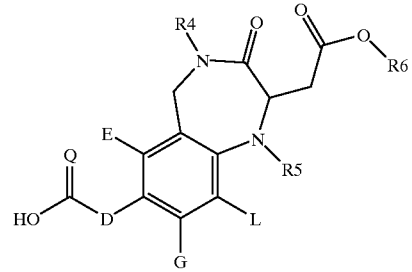

where b is first reacted in the presence of sulfonyl chloride, POCl$_3$ or PCl$_5$ to give the acid chloride and is then reacted with a in the presence of a base in an inert organic solvent, or a coupling of a with b is carried out by means of BOP or carbodiimide reagents, followed by a cyclization reaction which can be effected by means of heat, acids, bases, dehydrating substances and by addition of nucleophilic reagents, where, if appropriate, the COOR6 group is finally hydrolyzed and where Q in one of the two components (a) or (b) is oxygen and in the other component corresponds to Z, or (B) reaction of a component (a')

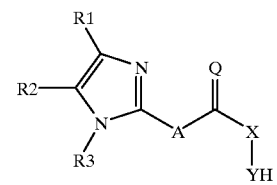

with a component (b)

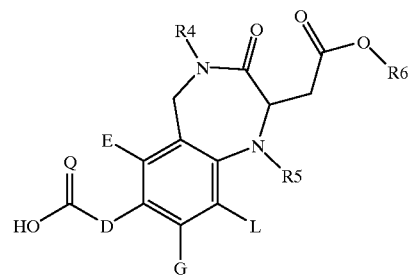

where b is first reacted in the presence of sulfonyl chloride, POCl$_3$ or PCl$_5$ to give the acid chloride and then reacted with a' in the presence of a base in an inert organic solvent, or a coupling of a' with b is carried out by means of BOP or carbodiimide reagents, followed by a cyclization reaction which can be effected by means of heat, acids, bases, dehydrating substances and by addition of generally nucleophilic reagents, where, if appropriate, the COOR6 group is finally hydrolyzed and where Q in one of the two components (a') or (b) is oxygen and in the other component corresponds to Z.

5. The process as claimed in claim 4, wherein in process variant (A), for component (a), X=N, Y=O and Q=NH and, for component (b), Q=O and in process variant (B), for component (a'), X=NH, Y=NH and Q=O and, for component (b), Q=O.

6. The process as claimed in claim 4, wherein R1 and R2 together with the formal double bond bridging them form a phenyl radical, R3, R5, E, G, L=H, R4, R6=methyl and A, D=a C—C single bond.

7. Method for the treatment of osteoporosis, restenosis, carcinoses and/or arteriosclerosis, said method comprising administering to a patient in need thereof an effective amount therefor of a compound according to any one of claims 1 to 3.

8. A pharmaceutical composition comprising at least one compound according to claim 1 and a pharmaceutically acceptable carrier.

* * * * *